United States Patent
Lee et al.

(10) Patent No.: US 11,992,643 B2
(45) Date of Patent: May 28, 2024

(54) NEUROVASCULAR INSERTION TOOL

(71) Applicant: NEURAVI LIMITED, Galway (IE)

(72) Inventors: Declan Lee, Galway (IE); Maeve Holian, Galway (IE)

(73) Assignee: NEURAVI LIMITED, Galway (IE)

( * ) Notice: Subject to any disclaimer, the term of this patent is extended or adjusted under 35 U.S.C. 154(b) by 767 days.

(21) Appl. No.: 17/119,601

(22) Filed: Dec. 11, 2020

(65) Prior Publication Data
US 2021/0187264 A1  Jun. 24, 2021

Related U.S. Application Data

(60) Provisional application No. 62/951,742, filed on Dec. 20, 2019.

(51) Int. Cl.
*A61M 39/02* (2006.01)
*A61M 39/06* (2006.01)
*A61B 17/22* (2006.01)
*A61B 17/34* (2006.01)
*A61M 25/10* (2013.01)

(52) U.S. Cl.
CPC ........ *A61M 39/0247* (2013.01); *A61M 39/06* (2013.01); *A61B 17/22* (2013.01); *A61B 17/3423* (2013.01); *A61M 25/104* (2013.01); *A61M 2039/0258* (2013.01); *A61M 2039/0626* (2013.01)

(58) Field of Classification Search
CPC .............. A61M 39/0247; A61M 39/06; A61M 2039/0258
See application file for complete search history.

(56) References Cited

U.S. PATENT DOCUMENTS

| | | | | |
|---|---|---|---|---|
| 6,251,085 B1 * | 6/2001 | Tezuka | .................. | A61M 25/09 604/524 |
| 8,162,855 B2 * | 4/2012 | Sakane | .................. | A61L 31/14 600/585 |
| 8,500,785 B2 * | 8/2013 | Gunderson | ......... | A61M 25/005 623/1.11 |
| 9,138,221 B2 * | 9/2015 | Hawkins | ............ | A61B 17/0401 |
| 9,144,667 B2 * | 9/2015 | Dolan | .................. | A61F 2/2433 |
| 2002/0165536 A1 | 11/2002 | Kelley et al. | | |

FOREIGN PATENT DOCUMENTS

EP    0 761 250 A1    3/1997

OTHER PUBLICATIONS

Extended European Search Report issued in European Patent Application No. 20 21 5379 dated Jun. 15, 2021.

* cited by examiner

*Primary Examiner* — Phong Son H Dang
(74) *Attorney, Agent, or Firm* — TROUTMAN PEPPER HAMILTON SANDERS LLP

(57) ABSTRACT

An improved insertion apparatus simplifies loading of neurovascular device into microcatheter. In one example, the insertion apparatus can include a tapered distal tip, allowing the insertion apparatus to reach the microcatheter with no gap. In another example, the insertion apparatus can include an uneven outer surface along its longitudinal body through laser ablation of material to form protrusions, forming taper features, forming wave patterns or thread extrusions.

10 Claims, 10 Drawing Sheets

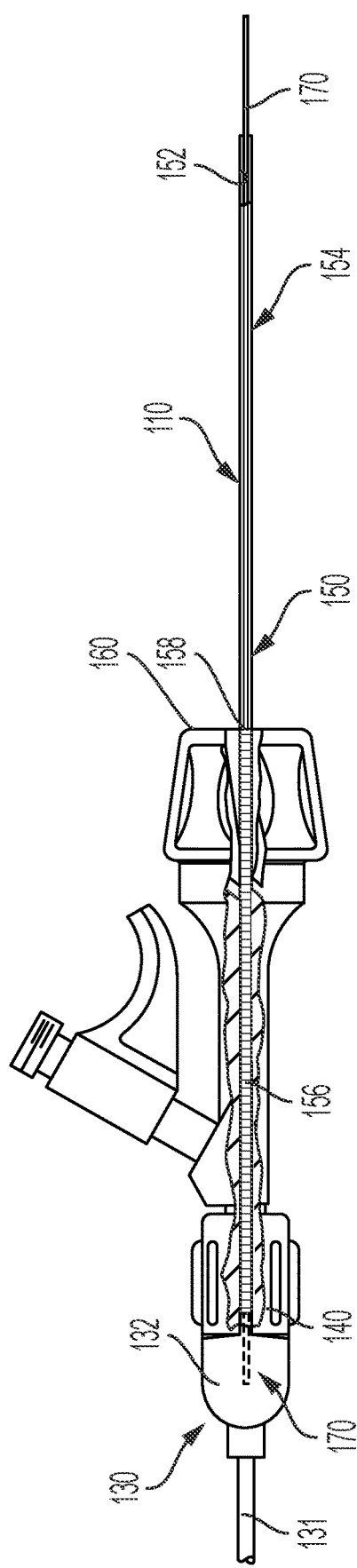
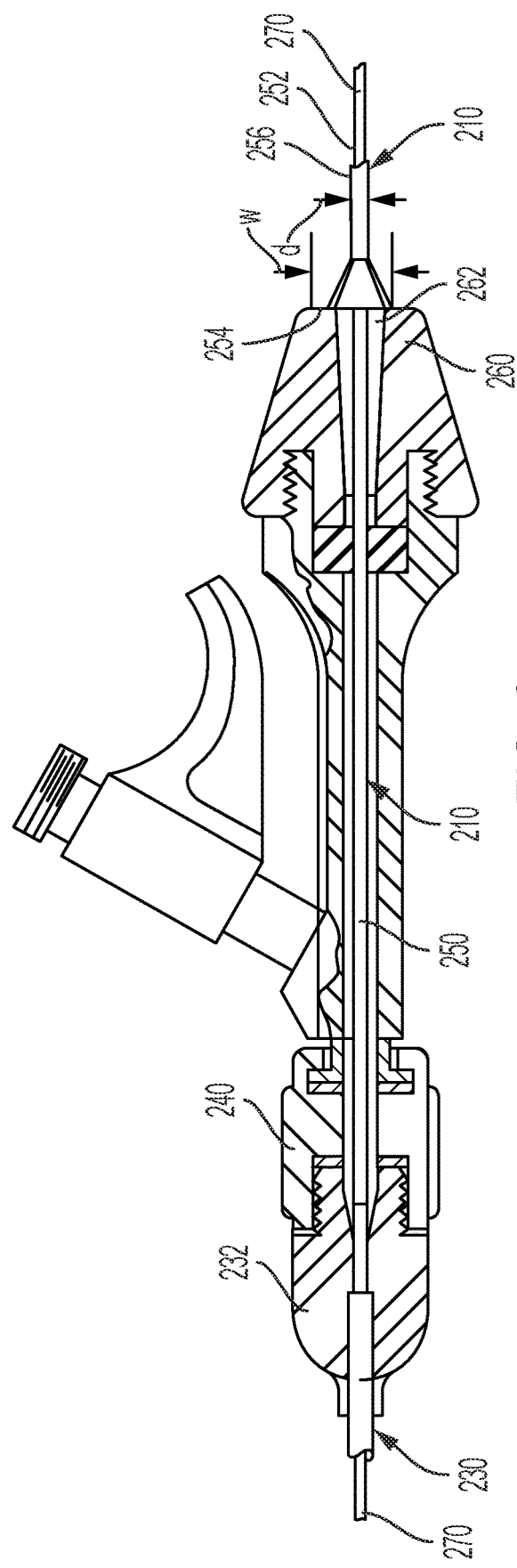
FIG. 1
FIG. 2

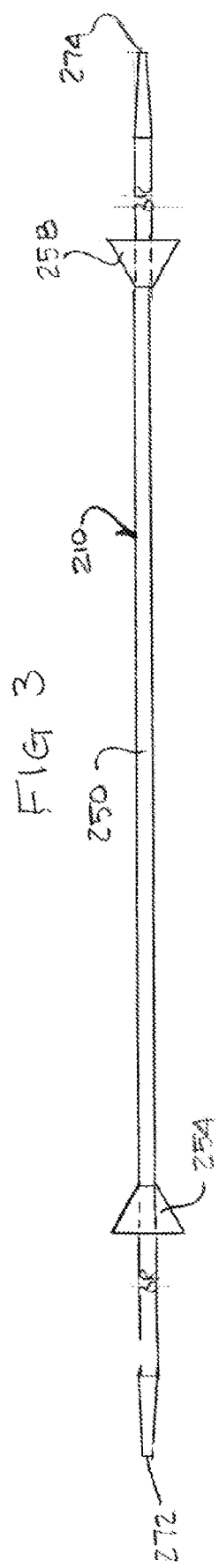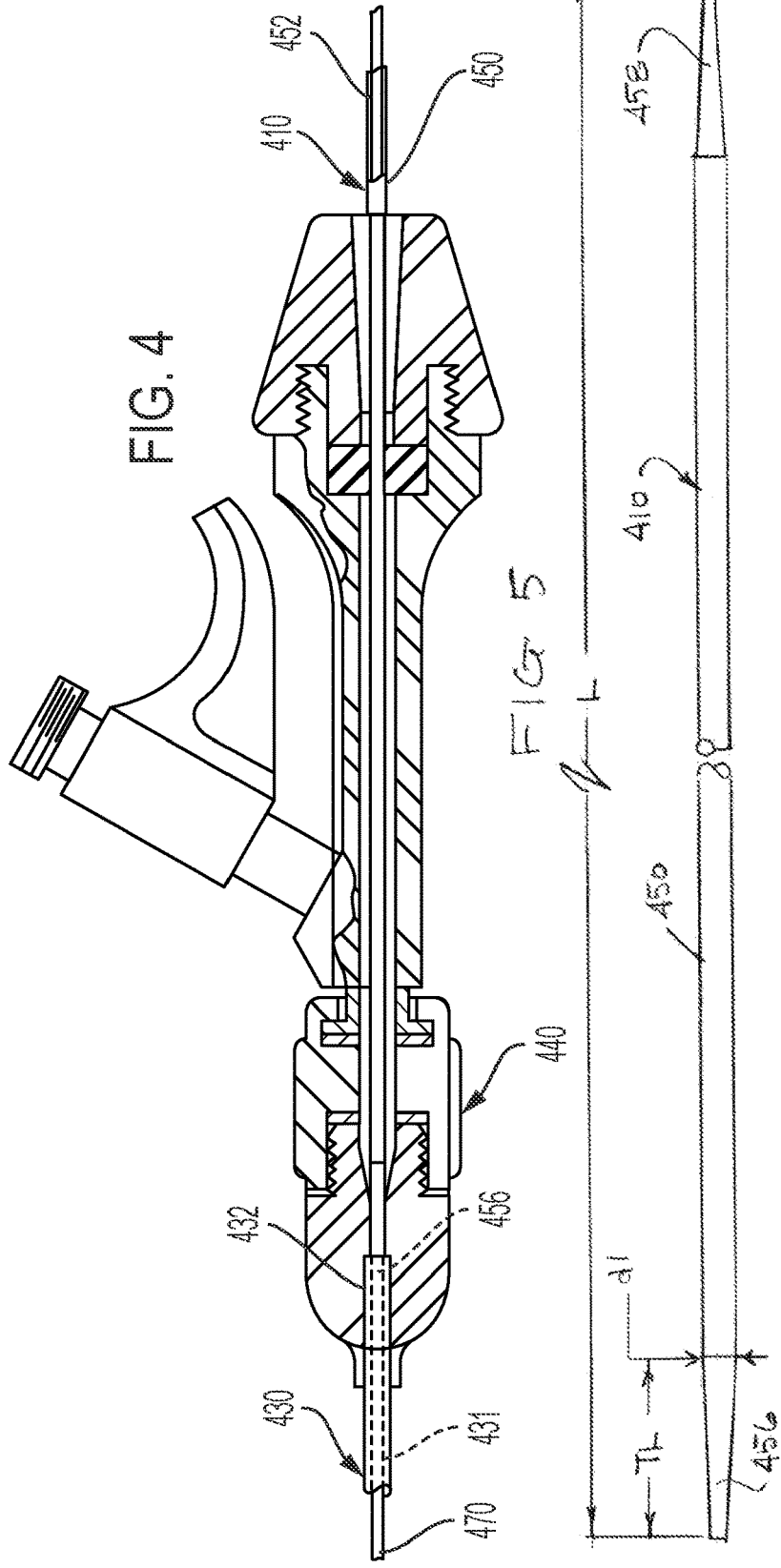

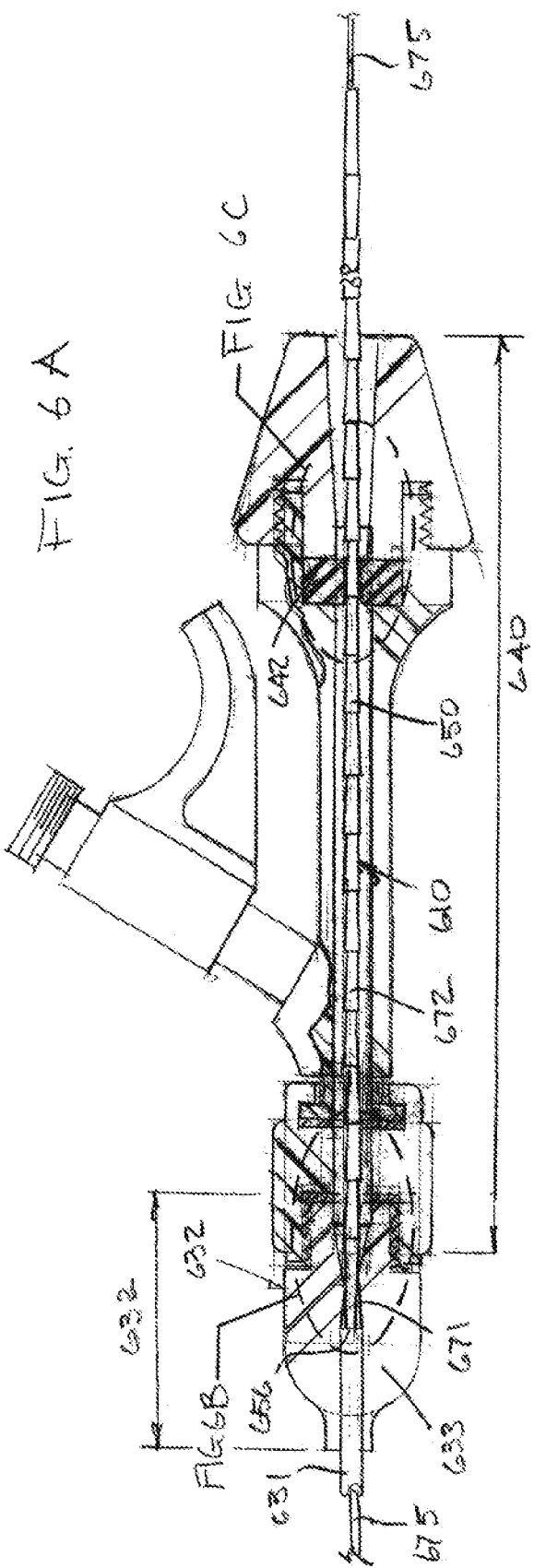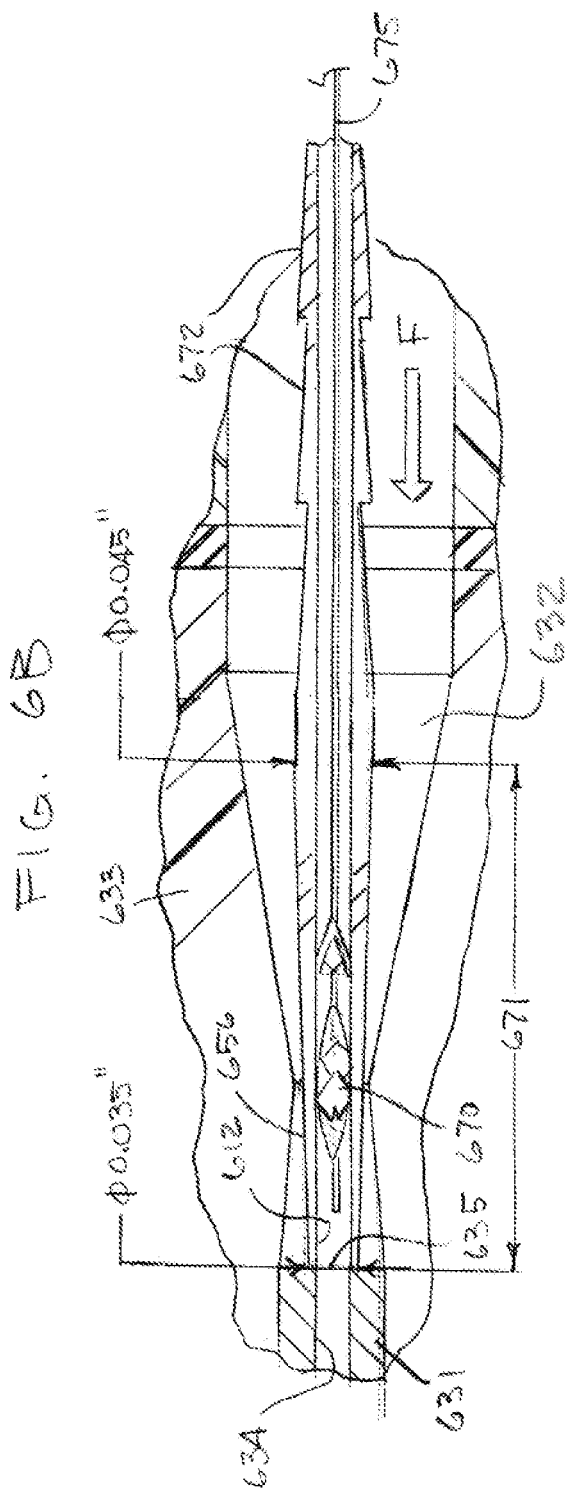

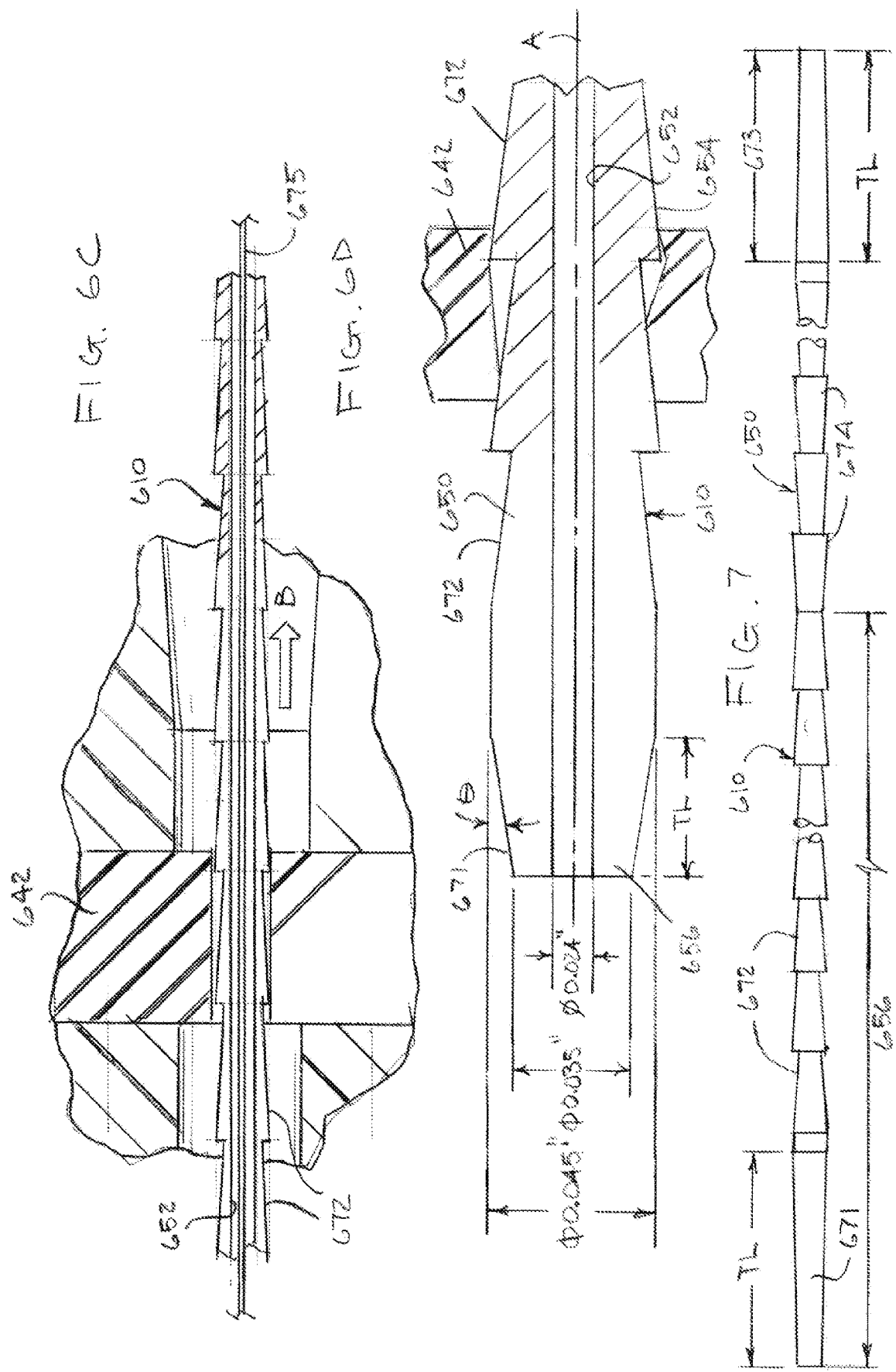

1200

1202 — Load a neurovascular device into an insertion apparatus

1204 — Attach an RHV to a microcatheter hub

1206 — Introduce the insertion apparatus into the RHV

1208 — Position the insertion apparatus tight against a face of the microcatheter

1210 — Close down an RHV seal on the insertion apparatus to hold the insertion apparatus in place

1212 — Move the neurovascular device forward from the insertion apparatus into the microcatheter until the neurovascular device is fully introduced into the microcatheter

1214 — Loosen the RHV seal to remove the insertion apparatus

1216 — Pull the insertion apparatus proximally off a shaft of the neurovascular device

FIG. 12

NEUROVASCULAR INSERTION TOOL

CROSS REFERENCE

This application claims priority of U.S. Provisional Application No. 62/951,742 filed Dec. 20, 2019. The entire contents of which are hereby incorporated by reference.

FIELD OF INVENTION

The present invention generally relates to intravascular medical treatments, and more particularly, to an insertion apparatus for introducing a neurovascular device into a microcatheter via a hemostasis valve.

BACKGROUND

Typically, during a thrombectomy procedure, an insertion tool is used to introduce a neurovascular device into a microcatheter via a hemostasis valve, such as a rotating hemostasis valve (RHV). Examples of the neurovascular device include, but not limited to, a mechanical thrombectomy device, a neurovascular access device, a neurovascular balloon device, a neurovascular assist device, and a neurovascular clot removal/flow device.

The hemostasis valve is attached to a proximal end of the microcatheter. The proximal end of the microcatheter includes a microcatheter hub that allows for the attachment of the hemostasis valve. The geometry of these microcatheter hubs vary in design and dimensions across commercial microcatheter designs. The neurovascular device is loaded into the microcatheter via the hemostasis valve by using the insertion tool. The insertion tool is advanced through the hemostasis valve into the microcatheter hub until it cannot be advanced any further. The neurovascular device is then tracked to the treatment location through the microcatheter. When loading the neurovascular device, the neurovascular device should not expand. In other words, the neurovascular device should remain in a wrapped state as it transitions from the insertion tool to the microcatheter.

However, it has been observed that during introduction of the neurovascular device, if the insertion tool is not positioned correctly, the neurovascular device does not load correctly into the microcatheter. For example, the insertion tool is prone to moving when introducing the neurovascular device into the microcatheter, when the hemostasis valve is not tight enough.

Further, the different microcatheter hub geometries result in a large variation in the distance that the insertion tool can be advanced into the microcatheter hub. If the insertion tool is too distal in the microcatheter, it can result in failed delivery of the neurovascular device which can potentially damage the neurovascular device. The different proximal hub geometries and hemostasis valve seals can also result in the insertion tool being pushed distally back out of the microcatheter hub. This can result in premature deployment of the neurovascular devices in the hemostasis valve resulting in a failed introduction, potentially damaging the device.

Due to the inaccurate placement of the insertion tool, the neurovascular device becomes damaged when being deployed in a hub of the microcatheter, rather than transitioning directly into a shaft of the microcatheter. The neurovascular device is then either thrown in the trash or returned to the manufacturer as a complaint unit.

There is a need for an improved insertion tool design that possesses geometric features that will make the insertion tool more universal and compatible with a range of microcatheter hub geometries that are commercially available. There is a need for an improved insertion tool design that reduces a gap between a distal tip of the insertion tool and the microcatheter in order to prevent potential snagging of the neurovascular device in the microcatheter hub. There is a need for an improved insertion tool design that reduces the possibility of the insertion tool backing out of the hemostasis valve during the introduction of the neurovascular device into the microcatheter. For example, there is a need for an improved surface finish of the insertion apparatus to improve grip on the hemostasis valve.

SUMMARY

It is an object of the present invention to provide systems, devices, and methods to meet the above-stated needs. Generally, it is an object of the present invention to provide an improved insertion apparatus that simplifies loading of neurovascular device into microcatheter. In one example, the insertion apparatus can include a tapered distal tip, allowing the insertion apparatus to reach the microcatheter with no gap. In another example, the insertion apparatus can include an uneven outer surface along its longitudinal body through laser ablation of material to form protrusions, forming taper features, forming wave patterns or thread extrusions.

An example insertion apparatus can introduce a neurovascular device into a microcatheter via the RHV. The example insertion apparatus can include a longitudinal body. The longitudinal body can define a lumen therethrough that allows the neurovascular device to pass through. The longitudinal body can include a proximal portion. The proximal portion can include a first color. The longitudinal body can include a distal portion. The distal portion can include a second color different from the first color. The longitudinal body can include a boundary between the proximal portion and the distal portion. The microcatheter can be first coupled to the RHV before introducing the insertion apparatus into the microcatheter. When the insertion apparatus is correctly positioned relative to the microcatheter and the RHV, the boundary can be aligned with a proximal end of the RHV Another example insertion apparatus for introducing a neurovascular device into a microcatheter via an RHV can include a longitudinal body. The longitudinal body can define a lumen therethrough that allows the neurovascular device to pass through. The insertion apparatus can include a ledge disposed on an outer surface of the longitudinal body that prevents a complete entry of the insertion apparatus into a proximal end of the RHV. The microcatheter can be first coupled to the RHV before introducing the insertion apparatus into the microcatheter. When the insertion apparatus is correctly positioned relative to the microcatheter and the RHV for introducing the neurovascular device into the microcatheter, the ledge can be aligned with the proximal end of the RHV.

The ledge can include a width greater than a diameter of an opening of the proximal end of the RHV. The diameter of the opening can allow a partial entry of the insertion apparatus into the proximal end of the RHV.

The ledge can be disposed towards a distal end of the longitudinal body. The insertion apparatus can include a second ledge disposed towards a proximal end of the longitudinal body.

Yet another example insertion apparatus for introducing a neurovascular device into a microcatheter via an RHV can include a longitudinal body. The longitudinal body can include a lumen therethrough that allows the neurovascular device to pass through. The longitudinal body can include a tapered distal portion sized to allow partial entry into a proximal end of a microcatheter shaft. The tapered distal portion can include an outer diameter sized to prevent complete deployment into the microcatheter. The outer diameter can be greater than 0.021 inches. The longitudinal body can include a tapered proximal portion. The tapered distal portion can include a length of approximately 10 mm.

A further example insertion apparatus for introducing a neurovascular device into a microcatheter via an RHV can include a longitudinal body. The longitudinal body can define a lumen therethrough that allows the neurovascular device to pass through. The insertion apparatus can include an uneven outer surface. The uneven outer surface can prevent a backward movement of the insertion apparatus from the microcatheter when introducing the neurovascular device into the microcatheter. A distal portion of the longitudinal body can include a distalmost taper to allow the distal portion to advance partially into the microcatheter. The uneven outer surface can include a sealing relationship with respect to a seal of the RHV. The uneven outer surface can define a plurality of tapers along a length of the longitudinal body to reduce movement of the insertion apparatus during introduction of the neurovascular device into the microcatheter. The plurality of tapers can include a first plurality of tapers inclined in a first direction at a first side of the insertion apparatus. The plurality of tapers can include a second plurality of tapers inclined in a second direction at a second side of the insertion apparatus. The second direction can be opposite from the first direction. The longitudinal body can define a length in a range from about 410 mm to about 600 mm. The RHV can further include a seal. The seal can include a recess formed in the seal. The uneven outer surface can include at least one threaded extrusion engaging with the recess formed in the seal of the RHV. The threaded extrusion can include a thickness less than a width of the recess formed in the seal of the RHV. The uneven outer surface can include a plurality of protrusions. At least one protrusion can include a length from about 2 mm to about 3 mm. The uneven outer surface can include a knurled surface. The uneven outer surface can include a wave pattern along a length of the longitudinal body. The RHV can further include a recess of a seal. The recess of the seal can include a complementary profile engaging with the uneven outer surface.

An example method for introducing a neurovascular device into a microcatheter via an RHV can include one or more of the following steps presented in no particular order. The method can include applying the RHV to the microcatheter. The method can include inserting an insertion apparatus into the microcatheter through the RHV. The method can include matching a boundary between a proximal portion and a distal portion of the insertion apparatus with a proximal end of the RHV. The proximal portion can include a first color. The distal portion can include a second color different from the first color. The method can include inserting the neurovascular device into the microcatheter through a lumen defined in the insertion apparatus.

Another example method for introducing a neurovascular device into a microcatheter via an RHV can include one or more of the following steps presented in no particular order. The method can include applying the RHV to the microcatheter. The method can include inserting an insertion apparatus into the microcatheter through the RHV. The method can include contacting a ledge disposed on an outer surface of a longitudinal body of the insertion apparatus to a proximal end of the RHV. The method can include inserting the neurovascular device into the microcatheter through a lumen defined in the insertion apparatus. The method can include defining a width of the ledge greater than a diameter of an opening of the proximal end of the RHV. The method can include allowing a partial entry of the insertion apparatus into the proximal end of the RHV based on the diameter of the opening.

Yet another example method for introducing a neurovascular device into a microcatheter via an RHV can include one or more of the following steps presented in no particular order. The method can include applying the RHV to the microcatheter. The method can include inserting a tapered distal portion of an insertion apparatus into a proximal end of a microcatheter shaft through the RHV. The method can include configuring the tapered distal portion to restrict full insertion of the tapered distal portion into the microcatheter. The method can include inserting the neurovascular device into the microcatheter through a lumen defined in the insertion apparatus.

A further example method for introducing a neurovascular device into a microcatheter via an RHV can include one or more of the following steps presented in no particular order. The method can include applying the RHV to the microcatheter. The method can include inserting a longitudinal body of an insertion apparatus into the microcatheter through the RHV. The method can include preventing a backward movement of the insertion apparatus from the microcatheter when introducing the neurovascular device into the microcatheter using an uneven outer surface of the longitudinal body. The method can include inserting the neurovascular device into the microcatheter through a lumen defined in the insertion apparatus.

All the example methods described above can include additional steps as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of an example insertion apparatus for introducing the neurovascular device into the microcatheter via the RHV according to aspects of the present invention.

FIG. 2 is an illustration of another example insertion apparatus for introducing the neurovascular device into the microcatheter via the RHV according to aspects of the present invention.

FIG. 3 is another illustration of the example insertion apparatus of FIG. 2 according to aspects of the present invention.

FIG. 4 is an illustration of yet another example insertion apparatus for introducing the neurovascular device into the microcatheter via the RHV according to aspects of the present invention.

FIG. 5 is another illustration of the example insertion apparatus of FIG. 4 according to aspects of the present invention.

FIG. 6A is an illustration of still another example insertion apparatus for introducing the neurovascular device into the microcatheter via the RHV according to aspects of the present invention.

FIG. 6B is another illustration of the example insertion apparatus of FIG. 6A according to aspects of the present invention.

FIG. 6C is still another illustration of the example insertion apparatus of FIG. 6A according to aspects of the present invention.

FIG. 6D is yet another illustration of the example insertion apparatus of FIG. 6A according to aspects of the present invention.

FIG. 7 is an additional illustration of the example insertion apparatus of FIG. 6A according to aspects of the present invention.

FIG. 12 is a flow chart illustrating steps for introducing the neurovascular device into the microcatheter via the insertion apparatus according to aspects of the present invention.

DETAILED DESCRIPTION

Figure 8:
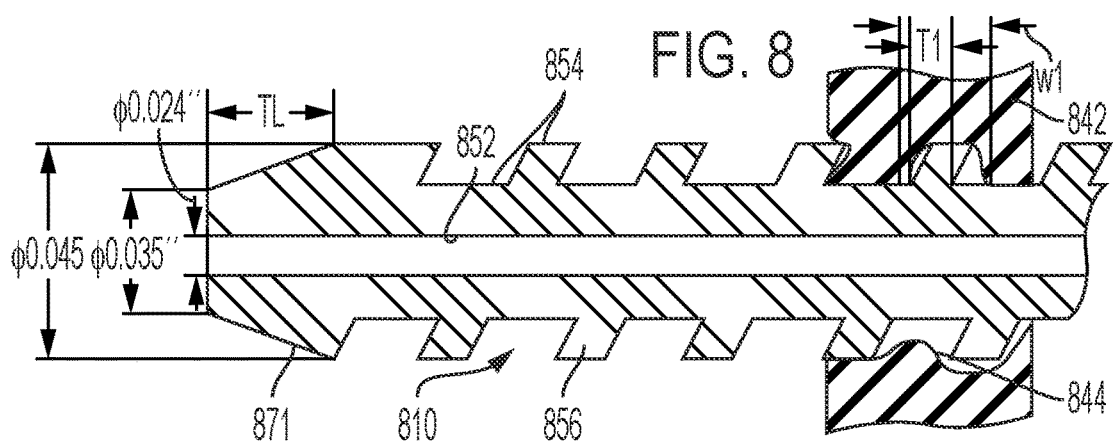
FIG. 8 is an illustration of a further example insertion apparatus for introducing the neurovascular device into the microcatheter via the RHV according to aspects of the present invention.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values ±20% of the recited value, e.g. "about 90%" can refer to the range of values from 71% to 99%.

An example of an insertion apparatus 110 is illustrated in FIG. 1 for introducing a neurovascular device 170 into a microcatheter 130 via an RHV 140. The microcatheter 130 can include a microcatheter shaft 131 and a microcatheter hub 132 that are all part of the same microcatheter assembly. Examples of the neurovascular device 170 can include, but not limited to, a mechanical thrombectomy device, a neurovascular access device, a neurovascular balloon device, a neurovascular assist device, and a neurovascular clot removal/flow device.

The insertion apparatus 110 can have a longitudinal body 150. The longitudinal body 150 can define a lumen 152 therethrough that allows the neurovascular device 170 to pass through. The longitudinal body 150 can include a proximal portion 154 having a first color and a distal portion 156 having a second color different from the first color. The longitudinal body 150 can include a boundary 158 between the proximal portion 154 and the distal portion 156. The boundary 158 can be aligned with a proximal end 160 of an RHV 140 when the insertion apparatus 110 is correctly positioned relative to the microcatheter 130 and the RHV 140, when the microcatheter 130 is coupled to the RHV 140.

Each end of the insertion apparatus 110 can be dyed a different color. This color change can allow the physician to know when the insertion apparatus 110 has been correctly positioned into the microcatheter hub 132. During loading, the physician can see if the insertion apparatus 110 begins to slip out of location based on color change. The color change can signify correct seating.

Another example of an insertion apparatus 210 is illustrated in FIG. 2 for introducing a neurovascular device 270 into a microcatheter 230 via an RHV 240. The insertion apparatus 210 can include a longitudinal body 250 defining a lumen 252 therethrough that allows the neurovascular device 270 to pass through. The insertion apparatus 210 can include a ledge 254 disposed on an outer surface 256 of the longitudinal body 250. Before introducing the neurovascular device 250 into the microcatheter 230, the microcatheter 230 can be first coupled to the RHV 240. When the insertion apparatus 210 is correctly positioned relative to the microcatheter 230 and the RHV 240 for introducing the neurovascular device 270 into the microcatheter 230, the ledge 254 can prevent a complete entry of the insertion apparatus 210 into a proximal end 260 of the RHV 240, when the ledge 254 is aligned with the proximal end 260 of the RHV 240.

As illustrated in FIG. 2, the ledge 254 can include a width "W" greater than a diameter "d" of an opening 262 of the proximal end 260 of the RHV 240. The diameter "d" of the opening 262 can allow a partial entry of the insertion apparatus 210 into the proximal end 260 of the RHV 240.

In one example as illustrated in FIG. 3, the ledge 254 can be disposed towards a distal end 272 of the longitudinal body 250. A second ledge 258 can be disposed towards a proximal end 274 of the longitudinal body 250. As such, the ledge can be positioned at each end of the insertion apparatus 210 to allow the physician to know when the insertion apparatus 210 has been correctly seated in the microcatheter hub 232. During loading, the physician can see if the insertion apparatus 210 begins to slip out of location when the ledge 254 or 258 does not sit directly at the correct location. In one example, at least one of the ledges 254, 258 can sit on the RHV 240.

Yet another example of an insertion apparatus 410 is illustrated in FIG. 4 for introducing a neurovascular device 470 into a microcatheter 430 via an RHV 440. The insertion apparatus 410 can include a longitudinal body 450. The longitudinal body 450 can include a lumen 452 therethrough that allows the neurovascular device 470 to pass through. The longitudinal body 450 can include a tapered distal portion 456 sized to allow partial entry into a proximal end 432 of a microcatheter shaft 431.

In one example as illustrated in FIG. 5, the tapered distal portion 456 can include an outer diameter "d1" sized to prevent complete deployment into the microcatheter 430.

In one example, the outer diameter "d1" can be greater than 0.021 inches, while an inner diameter of the microcatheter 430 can be approximately 0.021 inches or greater, so that the insertion apparatus 410 can be inserted into the microcatheter 430. The outer diameter "d1" can be greater than the inner diameter of the microcatheter 430 to prevent the insertion apparatus 410 sliding into the microcatheter 430. Preferably, an inner diameter of the insertion apparatus 410 can be greater than 0.021 inches to minimize loading forces. In one embodiment, the inner diameter of the microcatheter 430 can be in a range from 0.016 inches to 0.027 inches.

In one example, the tapered distal portion 456 can have a length "TL" of approximately 10 mm.

In one example as seen in FIG. 5, the longitudinal body 450 can include a tapered proximal portion 458.

The insertion apparatus 450 can be tapered on each end so that that each end can have an outer diameter "d1". The outer diameter "d1" can be greater than 0.021 inches to allow it to sit inside a lumen of the microcatheter 430. This can prevent the insertion apparatus 410 being inadvertently deployed in the microcatheter hub.

Referring to FIG. 5, the insertion apparatus 410 can have a length "L" in a range between approximately 410 mm and approximately 600 mm. The longitudinal body 650, 1150 can define the same length "L" in a range from about 410 mm to about 600 mm. In one example, the length "L" can be approximately 600 mm. Physicians can prefer to wrap the insertion apparatus around their hand while gripping the RHV. The length "L", such as 600 mm, can allow for a more secure grip while introducing the neurovascular device into the microcatheter.

A still another example of an insertion apparatus 610, 810, 910, 1010, 1110 is illustrated in FIGS. 6A-11 for introducing a neurovascular device 670 into a microcatheter 630 via an RHV 640. The insertion apparatus 610 can include a longitudinal body 650, 1150. The longitudinal body 650, 1150 can define a lumen 652, 852, 1152 therethrough that allows the neurovascular device 670 to pass through. The longitudinal body can include an uneven outer surface 654, 854, 954, 1154 preventing a backward movement of the insertion apparatus 610 from the microcatheter 630 when introducing the neurovascular device 670 into the microcatheter 630.

FIG. 6B can represent a longitudinal cross section of a full assembly of the insertion apparatus 610, the microcatheter 630 and the neurovascular device 670. As illustrated in FIG. 6B, the neurovascular device 670 can move forward into a microcatheter shaft 631 in a direction as represented by an arrow "F". In FIG. 6B, a shaded or hatched region enclosing the microcatheter shaft 631 and the microcatheter hub 632 can represent a microcatheter hub wall 633. As seen in FIG. 6B, the microcatheter shaft 631 can define a microcatheter shaft lumen 634 for receiving the neurovascular device 670.

In one example as illustrated in FIG. 6D, the insertion apparatus 610 can define a lumen 652 therein for accommodating the neurovascular device 670.

Preferably, the lumen 652 can have an inner diameter greater than 0.021 inches to minimize loading forces. In one embodiment, the lumen 652 can have an inner diameter of about 0.024 inches.

The insertion apparatus 610, 810, 910, 1010, 1110 can have one or more geometric features along its outer surface 654, 854, 954, 1154 to improve the contact between an RHV seal 642, 842, 1142 and the insertion apparatus. These geometric features can be a roughened outer surface on the insertion apparatus. The roughened outer surface can prevent the insertion apparatus 610, 810, 910, 1010, 1110 from moving distally back out of the microcatheter hub 632, therefore significantly reducing the possibility of a failed introduction or premature deployment of the neurovascular device 670.

In one example, a distal portion 656 of the longitudinal body 650 can include a distalmost taper 671 to allow the distal portion 656 to advance partially into the microcatheter 630. As shown in FIG. 6D, the distalmost taper 671 can form an angle θ in a range of approximately 10°-20° with respect to a longitudinal axis "A" of the insertion apparatus 610. The distalmost taper 671 can enable a distal tip of the insertion apparatus 610 to further advance into the microcatheter hub 632. The distalmost taper 671 can allow the insertion apparatus 610 to advance to a most distal end of the microcatheter hub 632, therefore significantly reducing the possibility of a failed delivery of the neurovascular device 670 into the microcatheter 630, which can otherwise occur due to a geometry of the microcatheter hub 632 or a partial deployment of the neurovascular device 670 in the microcatheter hub 632.

Figure 11:
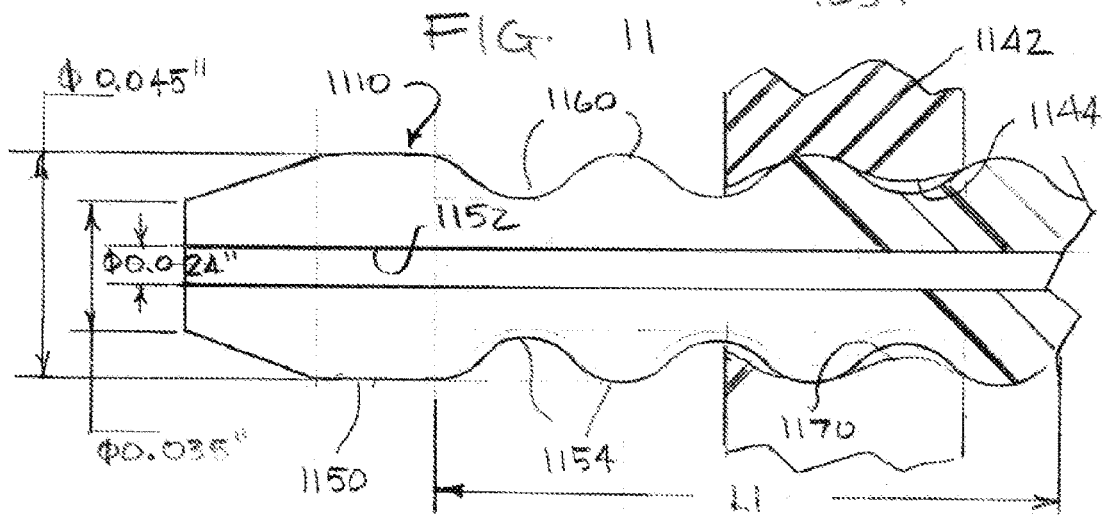
FIG. 11 is an illustration of a still further example insertion apparatus for introducing the neurovascular device into the microcatheter via the RHV according to aspects of the present invention.

In one example, with reference to FIG. 7, the longitudinal body 650 can have a proximal most taper 673. The distalmost taper 671 and the proximal most taper 673 each can have a length "TL" greater than 8.5 mm. In one example, the length "TL" can be approximately 10 mm. Each of the distalmost taper 671 and the proximal most taper 673 can taper from a maximum outer diameter of approximately 0.045 inches to a minimum outer diameter of approximately 0.035 inches as illustrated in FIGS. 6D, 8 and 11.

In one example, the uneven outer surface 654, 854 can form a sealing relationship with respect to a seal 642, 842, 1142 of the RHV 640.

In one example, the uneven outer surface 654 can include a plurality of tapers 672, 674 along the length of the insertion apparatus outer surface 654 to reduce movement of the insertion apparatus 610 during introduction of the neurovascular device 670 into the microcatheter 630. The plurality of tapers 672, 674 can be applied to both sides of the insertion apparatus to allow the insertion apparatus to be used from both sides. In one example, the plurality of tapers can include a first plurality of tapers 672 inclined in a first direction at a first side of the insertion apparatus 610, and a second plurality of tapers 674 inclined in a second direction at a second side of the insertion apparatus. The second direction can be opposite from the first direction. The tapers 672, 674 can server to reduce movement of the insertion apparatus when introducing the neurovascular device into the microcatheter.

In one example, the tapers 672 can be positioned at a distal end of the insertion apparatus 610, while tapers 674 can be positioned at a proximal end of the insertion apparatus 610. As illustrated in FIG. 7, the taper directions of tapers 672, 674 can be mirrored at a midpoint of the insertion apparatus, so that the insertion apparatus 610 can be used either way.

Each of the tapers 672, 674 along the length of the insertion apparatus can have a length shorter than the length "TL" of the distalmost taper 671 or the proximal most taper 673 in order to improve the grip the closed RHV seal 642 has on the insertion apparatus 610.

In one example as illustrated in FIG. 6C, when the RHV seal 642 closes on the insertion apparatus 610, tapers 672 or tapers 674 can be locked or gripped by the RHV seal 642 or embedded into the RHV seal 642 to provide additional grip, preventing the insertion apparatus 610 from backing out of RHV 640 during device delivery. The RHV seal 642 can close tight to the insertion apparatus outer diameter. The RHV seal 642 can deform to form a tight grip on the outer surface of the insertion apparatus 610. The RHV seal 642 can deflect to conform with the outer surface of the insertion apparatus 610. At this point, the RHV seal 642 can be tightened down onto the insertion apparatus 610 to aid holding it in place in the microcatheter hub. As a result, the insertion apparatus 610 can be prevented from backing out of the RHV 640 when introducing the neurovascular device 670 into the microcatheter 630.

With reference to FIG. 6C, tapers 672 or 674 can prevent the insertion apparatus 610 moving backwards in a direction as represented by an arrow "B" when introducing the neurovascular device 670 into the microcatheter shaft 631.

With reference to FIGS. 6D, 8 and 11, when the RHV seal 642 closes on the insertion apparatus 610, the RHV seal 642 can deform around the insertion apparatus 610 to form a firm grip on the insertion apparatus 610. As a result, the RHV seal 642 can prevent the insertion apparatus 610 from backing out of the RHV 640 when introducing the neurovascular device 670 into the microcatheter shaft 631.

In one example as illustrated in FIG. 8, the RHV 640 can include a seal 842. The seal 842 can include a recess 844 formed in the seal 842. The uneven outer surface 854 can include at least one threaded extrusion 856 engaging with the recess 844 formed in the seal 842 of the RHV 640.

In one example, the threaded extrusion 856 can include a thickness "T1" less than a width "W1" of the recess 844 formed in the seal 842 of the RHV 640.

Figure 9:
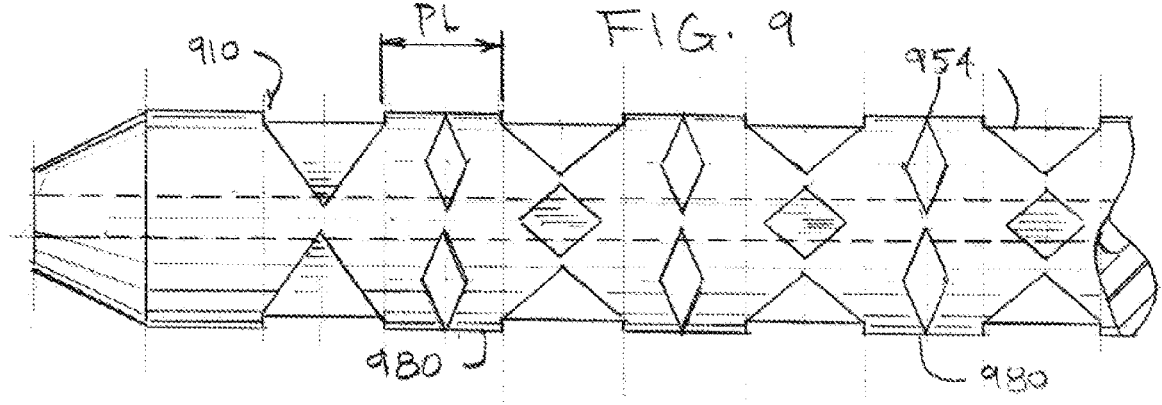
FIG. 9 is an illustration of a certain example insertion apparatus for introducing the neurovascular device into the microcatheter via the RHV according to aspects of the present invention.

In one example as illustrated in FIG. 9, laser engraved pattern on an outer surface of the insertion apparatus 910 can improve RHV grip, preventing movement. The uneven outer surface 954 can include a plurality of protrusions 980. At least one protrusion 980 can include a length "PL" from about 2 mm to about 3 mm. The length "PL" can be slightly small than an approximate size of the RHV seal.

Referring to FIG. 8, the threaded extrusion 856 can be formed along the outer surface of the insertion apparatus to improve tightness between the RHV seal and the insertion apparatus when the RHV seal grips the insertion apparatus.

Figure 10:
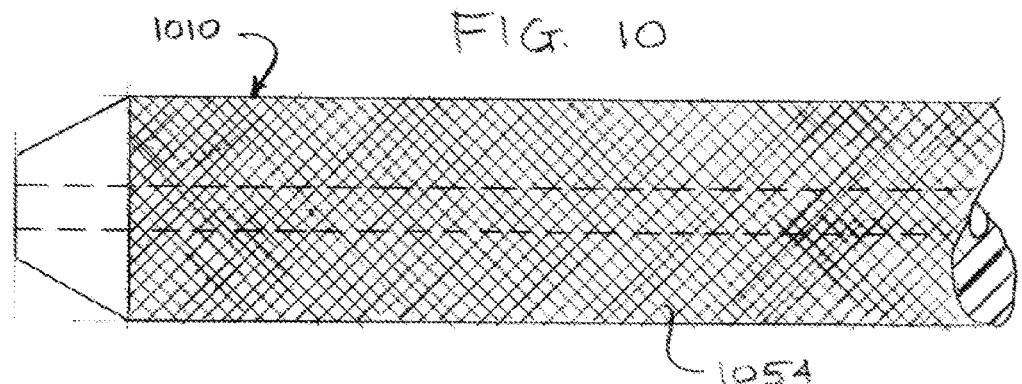
FIG. 10 is an illustration of an additional example insertion apparatus for introducing the neurovascular device into the microcatheter via the RHV according to aspects of the present invention.

In one example as illustrated in FIG. 10, the uneven outer surface 1054 can include a knurled surface to improve RHV grip.

In one example as illustrated in FIG. 11, the uneven outer surface 1154 can include a wave pattern 1160 along a length of the longitudinal body 1150 to improve grip of RHV on the insertion apparatus. The RHV seal 1142 can include a recess 1144. The recess 114 can include a complementary profile 1170 engaging with the uneven outer surface 1154. The RHV seal 1142 can be closed tight to the insertion apparatus 1110. The RHV seal 1142 is deformable to conform with the wave pattern 1160.

FIG. 12 is a flow diagram illustrating an example method 1200 for inserting the neurovascular device 670 into the microcatheter 630. The method 1200 can include one or more of the following steps presented in no particular order.

At step 1202, the neurovascular device 670 can be loaded into the insertion apparatus 610.

At step 1204, the RHV 640 can be attached to the microcatheter hub 632. A physician can apply the RHV 640 to the microcatheter hub 632 before inserting the insertion apparatus 610 into the microcatheter 630. In one example, in order to ensure that the below designs work correctly the RHV 640 of a specific length must be provided.

At step 1206, the insertion apparatus 610, with the neurovascular device 670 preloaded therein, can be introduced into the RHV 640.

At step 1208, the insertion apparatus 610 can be positioned tight against a proximal end 635 of a microcatheter shaft 631 as illustrated in FIG. 6B.

At step 1210, the RHV seal 642 can be closed down on the insertion apparatus 610 to hold the insertion apparatus 610 in place.

At step 1212, the neurovascular device 670 can be moved forward from the insertion apparatus 610 into the microcatheter 630 until the neurovascular device 670 is fully introduced into the microcatheter 630.

At step 1214, once the neurovascular device 670 is fully introduced into the microcatheter 630, the RHV seal 642 can be loosened in order to remove the insertion apparatus 670.

At step 1216, the insertion apparatus 670 can be pulled proximally off a shaft 675 of the neurovascular device 670.

Figure 13:
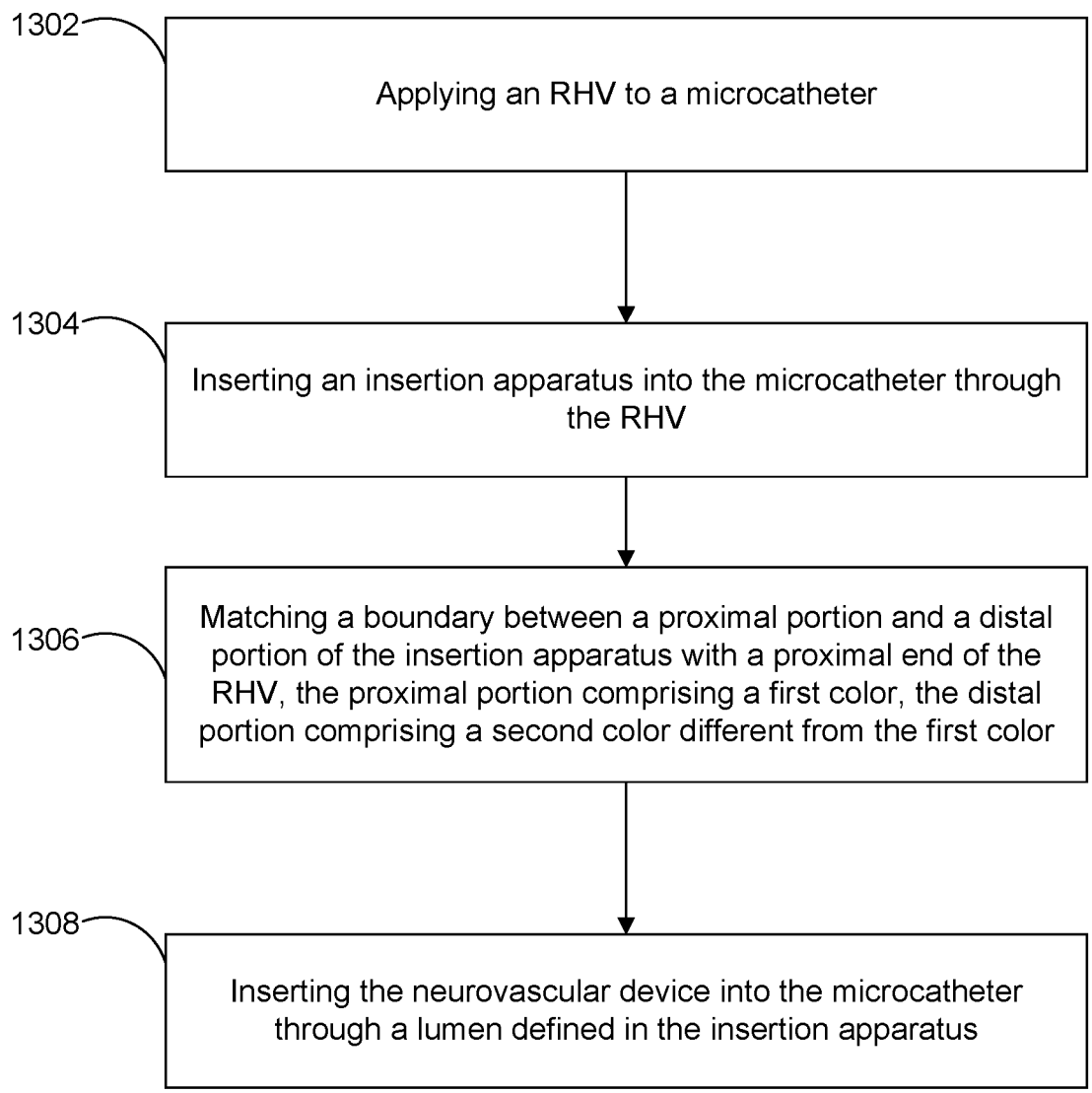
FIG. 13 is another flow chart illustrating steps for introducing the neurovascular device into the microcatheter via the RHV according to aspects of the present invention.

FIG. 13 is another flow diagram illustrating an example method 1300 for inserting the neurovascular device 170 into the microcatheter 130 via the RHV 140. The method 1300 can include one or more of the following steps presented in no particular order.

At step 1302, the RHV 140 can be applied to the microcatheter 130.

At step 1304, the insertion apparatus 110 can be inserted into the microcatheter 130 through the RHV 140.

At step 1306, the boundary 158 between the proximal portion 154 and the distal portion 156 of the insertion apparatus 110 can be matched with the proximal end 160 of the RHV 140. The proximal portion 154 can include a first color. The distal portion 156 can include a second color different from the first color.

At step 1308, the neurovascular device 170 can be inserted into the microcatheter 130 through the lumen 152 defined in the insertion apparatus 110.

Figure 14:
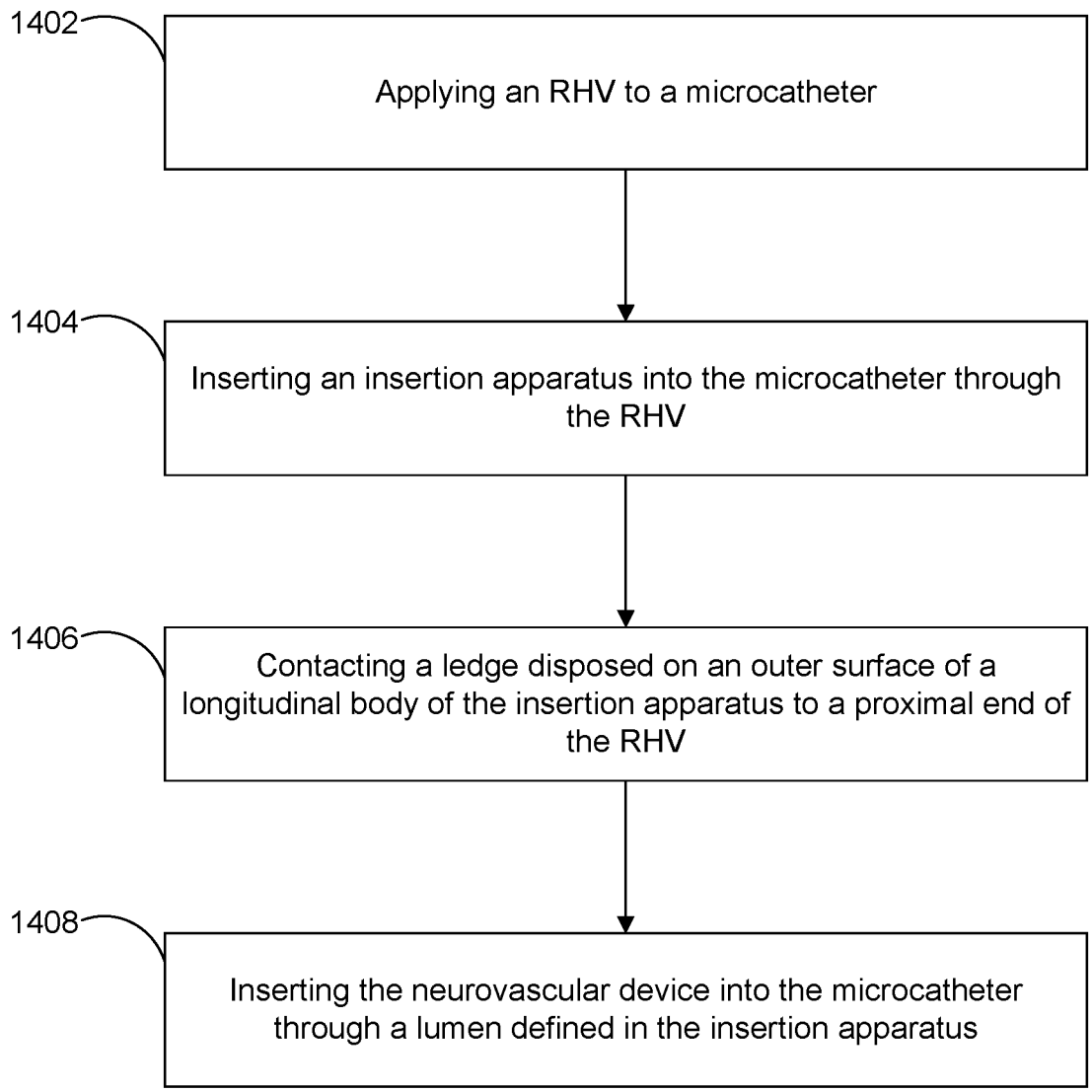
FIG. 14 is yet another flow chart illustrating steps for introducing the neurovascular device into the microcatheter via the RHV according to aspects of the present invention.

FIG. 14 is yet another flow diagram illustrating an example method 1400 for inserting the neurovascular device 270 into the microcatheter 230 via the RHV 240. The method 1400 can include one or more of the following steps presented in no particular order.

At step 1402, the RHV 240 can be applied to the microcatheter 230.

At step 1404, the insertion apparatus 210 can be inserted into the microcatheter 230 through the RHV 240.

At step 1406, the ledge 254 disposed on the outer surface 256 of the longitudinal body 250 of the insertion apparatus 210 can be contacted to the proximal end 260 of the RHV 240.

At step 1408, the neurovascular device 270 can be inserted into the microcatheter 230 through the lumen 252 defined in the insertion apparatus 210.

In one example, the ledge 254 can have a width "W" greater than a diameter "d" of the opening 262 of the proximal end 260 of the RHV 240, allowing a partial entry of the insertion apparatus 210 into the proximal end 260 of the RHV 240 based on the diameter "d" of the opening 262.

Figure 15:
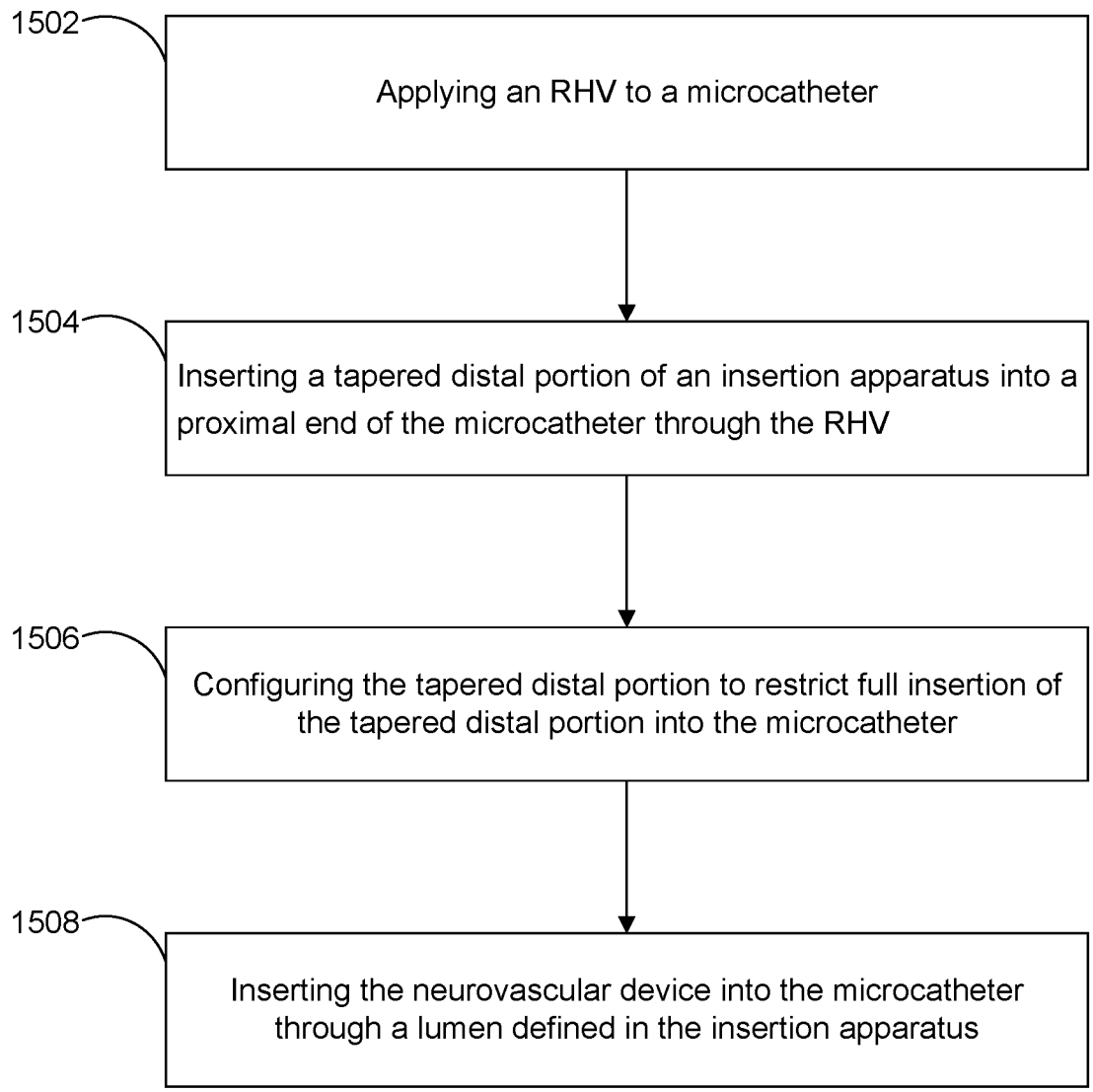
FIG. 15 is still another flow chart illustrating steps for introducing the neurovascular device into the microcatheter via the RHV according to aspects of the present invention.

FIG. 15 is a flow diagram illustrating an example method 1500 for introducing the neurovascular device 470 into the microcatheter 430 via the RHV 440. The method 1500 can include one or more of the following steps presented in no particular order.

At step 1502, the RHV 440 can be applied to the microcatheter 430.

At step 1504, the tapered distal portion 456 of the insertion apparatus 410 can be inserted into the proximal end 432 of the microcatheter shaft 431 through the RHV 440.

At step 1506, the tapered distal portion 456 can be configured to restrict full insertion of the tapered distal portion 456 into the microcatheter 430.

At step 1508, the neurovascular device 470 can be inserted into the microcatheter 430 through the lumen 452 defined in the insertion apparatus 410.

Figure 16:
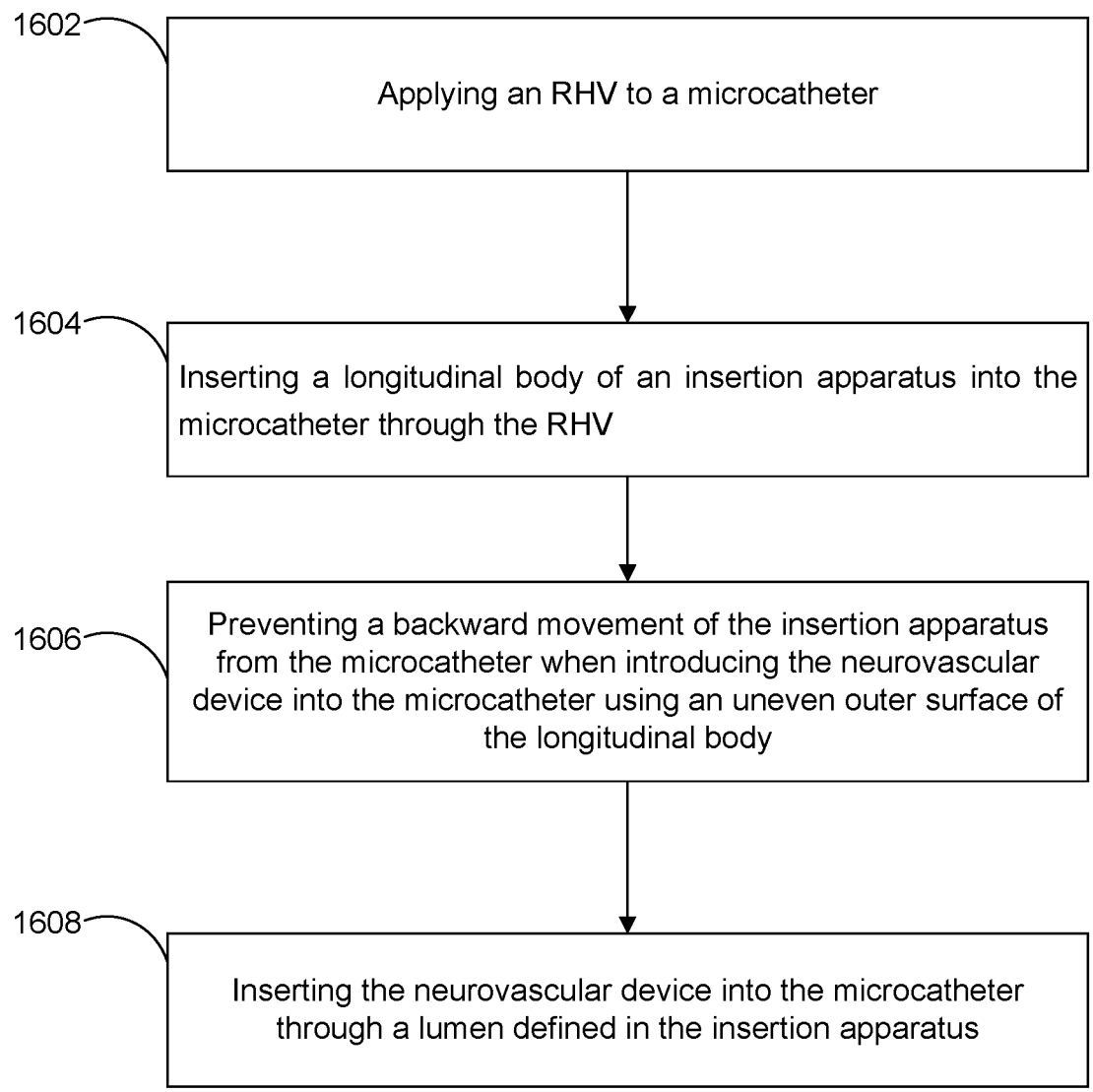
FIG. 16 is an additional flow chart illustrating steps for introducing the neurovascular device into the microcatheter via the RHV according to aspects of the present invention.

FIG. 16 is a flow diagram illustrating an example method 1600 for introducing the neurovascular device 670 into the microcatheter 630 via the RHV 640. The method 1600 can include one or more of the following steps presented in no particular order.

At step 1602, the RHV 640 can be applied to the microcatheter 630.

At step 1604, the longitudinal body 650, 1150 of the insertion apparatus 610, 810, 910, 1010, 1110 can be inserted into the microcatheter 630 through the RHV 640.

At step 1606, a backward movement of the insertion apparatus 610, 810, 910, 1010, 1110 can be prevented from the microcatheter 630 when introducing the neurovascular device 670 into the microcatheter 630 using the uneven outer surface 654, 854, 954, 1154 of the longitudinal body 650, 1150.

At step 1608, the neurovascular device 670 can be inserted into the microcatheter 630 through the lumen 652, 852, 1152 defined in the insertion apparatus 610, 810, 910, 1010, 1110.

Any of the example methods 1200, 1300, 1400, 1500 and 1600 can include additional steps as would be appreciated and understood by a person of ordinary skill in the art. The example method can be performed by an example system or a physician as disclosed herein, a variation thereof, or an alternative thereto as would be appreciated and understood by a person of ordinary skill in the art.

In one embodiment, the insertion apparatus may have a protrusion disposed on an outer surface of the insertion apparatus. The protrusion can form a spiral profile on the outer surface of the insertion apparatus. Both ends of the insertion apparatus may have a tapered profile to enhance ease of use and microcatheter capability.

The descriptions contained herein are examples of embodiments of the invention and are not intended in any way to limit the scope of the invention. As described herein, the invention contemplates many variations and modifications of the insertion apparatus. These modifications would be apparent to those having ordinary skill in the art to which this invention relates and are intended to be within the scope of the claims which follow.

What is claimed is:

1. An insertion apparatus for introducing a neurovascular device into a microcatheter via a rotating hemostasis valve (RHV), the insertion apparatus comprising:
a longitudinal body defining a lumen therethrough that allows the neurovascular device to pass through, and
an uneven outer surface preventing a backward movement of the insertion apparatus from the microcatheter when introducing the neurovascular device into the microcatheter wherein the RHV further comprises: a seal comprising with a recess formed in the seal; and wherein the uneven surface comprises at least one threaded extrusion engaging with the recess formed in the seal of the RHV.

2. The insertion apparatus of claim 1, wherein a distal portion of the longitudinal body comprises a distalmost taper to allow the distal portion to advance partially into the microcatheter.

3. The insertion apparatus of claim 1, wherein the uneven outer surface comprises a sealing relationship with respect to a seal of the RHV.

4. The insertion apparatus of claim 1, wherein the uneven outer surface defines a plurality of tapers along a length of the longitudinal body to reduce movement of the insertion apparatus during introduction of the neurovascular device into the microcatheter.

5. The insertion apparatus of claim 4, wherein the plurality of tapers comprises:
a first plurality of tapers inclined in a first direction at a first side of the insertion apparatus, and
a second plurality of tapers inclined in a second direction at a second side of the insertion apparatus, the second direction being opposite from the first direction.

6. The insertion apparatus of claim 1, wherein the longitudinal body defines a length in a range from about 410 mm to about 600 mm.

7. The insertion apparatus of claim 1, wherein the threaded extrusion comprises a thickness less than a width of the recess formed in the seal of the RHV.

8. The insertion apparatus of claim 7, wherein the uneven outer surface comprises a plurality of protrusions, and wherein at least one protrusion comprises a length from about 2 mm to about 3 mm.

9. The insertion apparatus of claim 1, wherein the uneven outer surface comprises a knurled surface.

10. The insertion apparatus of claim 1, wherein the uneven outer surface comprises a wave pattern along a length of the longitudinal body, and
wherein the RHV further comprises a recess of a seal comprising a complementary profile engaging with the uneven outer surface.

* * * * *